(12) United States Patent
Besko et al.

(10) Patent No.: US 8,781,548 B2
(45) Date of Patent: Jul. 15, 2014

(54) MEDICAL SENSOR WITH FLEXIBLE COMPONENTS AND TECHNIQUE FOR USING THE SAME

(75) Inventors: David Besko, Thornton, CO (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 674 days.

(21) Appl. No.: 12/722,355

(22) Filed: Mar. 11, 2010

(65) Prior Publication Data

US 2010/0249557 A1 Sep. 30, 2010

Related U.S. Application Data

(60) Provisional application No. 61/165,269, filed on Mar. 31, 2009.

(51) Int. Cl.
*A61B 5/1455* (2006.01)

(52) U.S. Cl.
USPC ............ 600/344; 600/310; 600/324; 600/322

(58) Field of Classification Search
USPC .................................. 600/309–344
See application file for complete search history.

(56) References Cited

U.S. PATENT DOCUMENTS

| | | |
|---|---|---|
| 4,025,733 A | 5/1977 | Klar et al. |
| 4,047,400 A | 9/1977 | Thorneburg |
| 4,462,116 A | 7/1984 | Sanzone et al. |
| 4,499,741 A | 2/1985 | Harris |
| 4,510,938 A | 4/1985 | Jobsis et al. |
| 4,570,638 A | 2/1986 | Stoddart et al. |
| 4,675,919 A | 6/1987 | Heine et al. |
| 4,685,464 A | 8/1987 | Goldberger et al. |
| 4,739,757 A | 4/1988 | Edwards |
| 4,775,116 A | 10/1988 | Klein |
| 4,784,162 A | 11/1988 | Ricks et al. |
| 4,802,485 A | 2/1989 | Bowers et al. |
| 4,833,734 A | 5/1989 | Der Estephanian |
| 4,838,279 A | 6/1989 | Fore |
| 4,856,116 A | 8/1989 | Sullivan |
| 4,890,619 A | 1/1990 | Hatschek |
| 4,910,804 A | 3/1990 | Lidgren |

(Continued)

FOREIGN PATENT DOCUMENTS

| | | |
|---|---|---|
| CN | 1306260 | 8/2001 |
| CN | 1657007 | 8/2005 |

(Continued)

OTHER PUBLICATIONS

Soto, Denise A.; "A Comparative Study of Pulse Oximeter Measurements: Digit Versus Earlobe," Master of Science Thesis, California State University Dominguez Hills, May 1997, 46 pgs.

(Continued)

*Primary Examiner* — Eric Winakur
*Assistant Examiner* — Marjan Fardanesh
(74) *Attorney, Agent, or Firm* — Fletcher Yoder PC

(57) ABSTRACT

According to various embodiments, a hat-based or headband sensor assembly may include thin or flexible optical sensing components, such as optical fibers or ultra thin emitters or detectors. In embodiments, the sensor assembly may be a hat-based sensor that includes a gripping region, for example on the inside of the hat band, to help secure the hat to a patient's head.

11 Claims, 4 Drawing Sheets

(56) References Cited

U.S. PATENT DOCUMENTS

| | | |
|---|---|---|
| 4,918,758 A | 4/1990 | Rendina |
| 4,930,888 A | 6/1990 | Freisleben et al. |
| 4,942,877 A | 7/1990 | Sakai et al. |
| 4,972,331 A | 11/1990 | Chance |
| 4,977,011 A | 12/1990 | Smith |
| 4,991,234 A | 2/1991 | Greenberg |
| 4,996,975 A | 3/1991 | Nakamura |
| 5,005,374 A | 4/1991 | Spitler et al. |
| 5,054,488 A | 10/1991 | Muz |
| 5,080,096 A | 1/1992 | Hooper et al. |
| 5,080,098 A | 1/1992 | Willett et al. |
| H1039 H | 4/1992 | Tripp, Jr. et al. |
| 5,111,817 A | 5/1992 | Clark et al. |
| 5,119,815 A | 6/1992 | Chance |
| 5,122,974 A | 6/1992 | Chance |
| 5,125,403 A | 6/1992 | Culp |
| 5,167,230 A | 12/1992 | Chance |
| 5,188,108 A | 2/1993 | Secker |
| 5,191,891 A | 3/1993 | Righter |
| 5,214,409 A | 5/1993 | Beigel |
| 5,217,013 A | 6/1993 | Lewis et al. |
| 5,224,478 A | 7/1993 | Sakai et al. |
| 5,237,994 A | 8/1993 | Goldberger et al. |
| 5,241,300 A | 8/1993 | Buschmann |
| 5,246,003 A | 9/1993 | DeLonzor |
| 5,253,645 A | 10/1993 | Friedman et al. |
| 5,263,244 A | 11/1993 | Centa et al. |
| 5,267,563 A | 12/1993 | Swedlow et al. |
| 5,267,567 A | 12/1993 | Aung et al. |
| 5,295,490 A | 3/1994 | Dodakian |
| 5,313,940 A | 5/1994 | Fuse et al. |
| 5,337,744 A | 8/1994 | Brianigan |
| 5,348,008 A | 9/1994 | Bornn et al. |
| 5,353,798 A | 10/1994 | Sieben |
| 5,354,979 A | 10/1994 | Adelson et al. |
| 5,357,953 A | 10/1994 | Merrick et al. |
| 5,368,025 A | 11/1994 | Young et al. |
| 5,368,562 A | 11/1994 | Blomquist et al. |
| 5,383,874 A | 1/1995 | Jackson et al. |
| 5,392,777 A | 2/1995 | Swedlow et al. |
| 5,398,689 A | 3/1995 | Connor et al. |
| 5,400,267 A | 3/1995 | Denen et al. |
| 5,405,269 A | 4/1995 | Stupecky |
| 5,405,614 A | 4/1995 | D'Angelo et al. |
| 5,413,101 A | 5/1995 | Sugiura |
| 5,413,102 A | 5/1995 | Schmidt et al. |
| 5,415,166 A | 5/1995 | Imran |
| 5,427,093 A | 6/1995 | Ogawa et al. |
| 5,431,170 A | 7/1995 | Mathews |
| 5,437,275 A | 8/1995 | Amundsen et al. |
| 5,437,634 A | 8/1995 | Amano |
| 5,438,986 A | 8/1995 | Disch et al. |
| 5,444,254 A | 8/1995 | Thomson |
| 5,451,763 A | 9/1995 | Pickett et al. |
| 5,469,845 A | 11/1995 | DeLonzor et al. |
| 5,482,034 A | 1/1996 | Lewis et al. |
| 5,490,523 A | 2/1996 | Isaacson et al. |
| 5,528,519 A | 6/1996 | Ohkura et al. |
| 5,546,955 A | 8/1996 | Wilk |
| 5,551,423 A | 9/1996 | Sugiura |
| 5,562,718 A | 10/1996 | Palermo |
| 5,564,108 A | 10/1996 | Hunsaker et al. |
| 5,564,417 A | 10/1996 | Chance |
| 5,584,296 A | 12/1996 | Cui et al. |
| 5,592,408 A | 1/1997 | Keskin et al. |
| 5,596,987 A | 1/1997 | Chance |
| 5,617,865 A | 4/1997 | Palczewska et al. |
| 5,617,866 A | 4/1997 | Marian, Jr. |
| 5,627,323 A | 5/1997 | Stern |
| 5,634,466 A | 6/1997 | Gruner |
| 5,638,593 A | 6/1997 | Gerhardt et al. |
| 5,640,953 A | 6/1997 | Bishop et al. |
| 5,645,440 A | 7/1997 | Tobler et al. |
| 5,645,586 A | 7/1997 | Meltzer |
| 5,646,416 A | 7/1997 | Van De Velde |
| 5,671,750 A | 9/1997 | Shinoda |
| 5,673,708 A | 10/1997 | Athanasiou et al. |
| 5,680,857 A | 10/1997 | Pelikan et al. |
| 5,681,285 A | 10/1997 | Ford et al. |
| 5,683,434 A | 11/1997 | Archer |
| 5,697,363 A | 12/1997 | Hart |
| 5,697,367 A | 12/1997 | Lewis et al. |
| 5,701,894 A | 12/1997 | Cherry et al. |
| 5,706,820 A | 1/1998 | Hossack et al. |
| 5,709,205 A | 1/1998 | Bukta |
| 5,732,475 A | 3/1998 | Sacks et al. |
| 5,738,612 A | 4/1998 | Tsuda |
| 5,743,856 A | 4/1998 | Oka et al. |
| 5,743,857 A | 4/1998 | Shinoda et al. |
| 5,752,913 A | 5/1998 | Oka |
| 5,752,920 A | 5/1998 | Ogura et al. |
| 5,758,644 A | 6/1998 | Diab et al. |
| 5,772,601 A | 6/1998 | Oka et al. |
| 5,776,058 A | 7/1998 | Levinson et al. |
| 5,776,071 A | 7/1998 | Inukai et al. |
| 5,779,631 A | 7/1998 | Chance |
| 5,779,639 A | 7/1998 | Yeung |
| 5,782,757 A | 7/1998 | Diab et al. |
| 5,786,592 A | 7/1998 | Hök |
| 5,791,347 A | 8/1998 | Flaherty et al. |
| 5,791,348 A | 8/1998 | Aung et al. |
| 5,792,052 A | 8/1998 | Isaacson et al. |
| 5,792,058 A | 8/1998 | Lee et al. |
| 5,797,841 A | 8/1998 | Delonzor et al. |
| 5,810,724 A | 9/1998 | Gronvall |
| 5,813,980 A | 9/1998 | Levinson et al. |
| 5,823,012 A | 10/1998 | Hacskaylo |
| 5,823,952 A | 10/1998 | Levinson et al. |
| 5,826,277 A | 10/1998 | McConville |
| 5,830,137 A | 11/1998 | Scharf et al. |
| 5,830,148 A | 11/1998 | Inukai et al. |
| 5,830,149 A | 11/1998 | Oka et al. |
| 5,833,602 A | 11/1998 | Osemwota |
| 5,836,887 A | 11/1998 | Oka et al. |
| 5,839,439 A | 11/1998 | Nierlich et al. |
| RE36,000 E | 12/1998 | Swedlow et al. |
| 5,842,981 A | 12/1998 | Larsen et al. |
| 5,842,982 A | 12/1998 | Mannheimer |
| 5,851,179 A | 12/1998 | Ritson et al. |
| 5,857,974 A | 1/1999 | Eberle et al. |
| 5,860,932 A | 1/1999 | Goto et al. |
| 5,860,957 A | 1/1999 | Jacobsen et al. |
| 5,868,133 A | 2/1999 | DeVries et al. |
| 5,870,626 A | 2/1999 | Lebeau |
| 5,872,713 A | 2/1999 | Douglas et al. |
| 5,873,821 A | 2/1999 | Chance et al. |
| 5,879,294 A | 3/1999 | Anderson et al. |
| 5,891,021 A | 4/1999 | Dillon et al. |
| 5,895,359 A | 4/1999 | Peel |
| 5,902,235 A | 5/1999 | Lewis et al. |
| 5,906,581 A | 5/1999 | Tsuda |
| 5,916,154 A | 6/1999 | Hobbs et al. |
| 5,931,790 A | 8/1999 | Peel |
| 5,931,791 A | 8/1999 | Saltzstein et al. |
| 5,934,925 A | 8/1999 | Tobler et al. |
| 5,936,539 A | 8/1999 | Fuchs |
| 5,947,905 A | 9/1999 | Hadjicostis et al. |
| 5,954,053 A | 9/1999 | Chance et al. |
| 5,957,850 A | 9/1999 | Marian, Jr. et al. |
| 5,964,701 A | 10/1999 | Asada et al. |
| 5,980,464 A | 11/1999 | Tsuda |
| 5,983,129 A | 11/1999 | Cowan et al. |
| 5,987,343 A | 11/1999 | Kinast |
| 5,987,351 A | 11/1999 | Chance |
| 5,991,648 A | 11/1999 | Levin |
| 5,995,077 A | 11/1999 | Wilcox et al. |
| 5,995,855 A | 11/1999 | Kiani et al. |
| 5,995,856 A | 11/1999 | Mannheimer et al. |
| 5,995,857 A | 11/1999 | Toomim et al. |
| 5,999,834 A | 12/1999 | Wang et al. |
| 6,007,492 A | 12/1999 | Goto et al. |
| 6,011,986 A | 1/2000 | Diab et al. |
| 6,022,320 A | 2/2000 | Ogura et al. |
| 6,027,453 A | 2/2000 | Miwa et al. |

(56) References Cited

U.S. PATENT DOCUMENTS

| | | |
|---|---|---|
| 6,030,351 A | 2/2000 | Schmidt et al. |
| 6,031,603 A | 2/2000 | Fine et al. |
| 6,036,651 A | 3/2000 | Inukai et al. |
| 6,041,247 A | 3/2000 | Weckstrom et al. |
| 6,047,201 A | 4/2000 | Jackson |
| 6,047,203 A | 4/2000 | Sackner et al. |
| 6,049,958 A | 4/2000 | Eberle et al. |
| 6,050,951 A | 4/2000 | Friedman et al. |
| 6,052,619 A | 4/2000 | John |
| 6,084,380 A | 7/2000 | Burton |
| 6,085,752 A | 7/2000 | Kehr et al. |
| 6,106,780 A | 8/2000 | Douglas et al. |
| 6,115,621 A | 9/2000 | Chin |
| 6,118,382 A | 9/2000 | Hibbs et al. |
| 6,134,459 A | 10/2000 | Roberts et al. |
| 6,144,868 A | 11/2000 | Parker |
| 6,149,481 A | 11/2000 | Wang et al. |
| 6,152,754 A | 11/2000 | Gerhardt et al. |
| 6,154,667 A | 11/2000 | Miura et al. |
| 6,162,188 A | 12/2000 | Barnea |
| 6,165,173 A | 12/2000 | Kamdar et al. |
| 6,171,258 B1 | 1/2001 | Katakasoglu et al. |
| 6,173,196 B1 | 1/2001 | Delonzor et al. |
| 6,179,786 B1 | 1/2001 | Young |
| 6,181,959 B1 | 1/2001 | Schollermann et al. |
| 6,184,521 B1 | 2/2001 | Coffin, IV et al. |
| 6,186,953 B1 | 2/2001 | Narimatsu |
| 6,186,954 B1 | 2/2001 | Narimatsu |
| 6,190,325 B1 | 2/2001 | Narimatsu |
| 6,195,575 B1 | 2/2001 | Levinson |
| 6,196,974 B1 | 3/2001 | Miwa |
| 6,198,952 B1 | 3/2001 | Miesel |
| 6,199,550 B1 | 3/2001 | Wiesmann et al. |
| 6,209,144 B1 | 4/2001 | Carter |
| 6,213,952 B1 | 4/2001 | Finarov et al. |
| 6,216,021 B1 | 4/2001 | Franceschini et al. |
| 6,223,063 B1 | 4/2001 | Chaiken et al. |
| 6,241,680 B1 | 6/2001 | Miwa |
| 6,248,083 B1 | 6/2001 | Smith et al. |
| 6,251,076 B1 | 6/2001 | Hovland et al. |
| 6,251,080 B1 | 6/2001 | Henkin et al. |
| 6,251,081 B1 | 6/2001 | Narimatsu |
| 6,251,113 B1 | 6/2001 | Appelbaum et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,263,221 B1 | 7/2001 | Chance et al. |
| 6,263,223 B1 | 7/2001 | Shepherd et al. |
| 6,280,213 B1 | 8/2001 | Tobler et al. |
| 6,282,450 B1 | 8/2001 | Hartlaub et al. |
| 6,283,922 B1 | 9/2001 | Goto et al. |
| 6,285,895 B1 | 9/2001 | Ristolainen et al. |
| 6,306,076 B1 | 10/2001 | Gill |
| 6,308,089 B1 | 10/2001 | von der Ruhr et al. |
| 6,321,100 B1 | 11/2001 | Parker |
| 6,322,516 B1 | 11/2001 | Masuda et al. |
| 6,343,223 B1 | 1/2002 | Chin et al. |
| 6,343,224 B1 | 1/2002 | Parker |
| 6,346,886 B1 | 2/2002 | De La Huerga |
| 6,349,228 B1 | 2/2002 | Kiani et al. |
| 6,356,774 B1 | 3/2002 | Bernstein et al. |
| 6,362,622 B1 | 3/2002 | Stauber et al. |
| 6,368,282 B1 | 4/2002 | Oka et al. |
| 6,370,411 B1 | 4/2002 | Osadchy et al. |
| 6,377,829 B1 | 4/2002 | Al-Ali |
| 6,381,480 B1 | 4/2002 | Stoddart et al. |
| 6,381,481 B1 | 4/2002 | Levendowski et al. |
| 6,385,486 B1 | 5/2002 | John et al. |
| 6,387,092 B1 | 5/2002 | Burnside et al. |
| 6,388,240 B2 | 5/2002 | Schulz et al. |
| 6,397,091 B2 | 5/2002 | Diab et al. |
| 6,405,075 B1 | 6/2002 | Levin |
| 6,416,471 B1 | 7/2002 | Kumar et al. |
| 6,416,474 B1 | 7/2002 | Penner et al. |
| 6,417,774 B1 | 7/2002 | Hibbs et al. |
| 6,423,010 B1 | 7/2002 | Friedman et al. |
| 6,430,423 B2 | 8/2002 | DeLonzor et al. |
| 6,432,050 B1 | 8/2002 | Porat et al. |
| 6,450,168 B1 | 9/2002 | Nguyen |
| 6,450,957 B1 | 9/2002 | Yoshimi et al. |
| 6,450,981 B1 | 9/2002 | Shabty et al. |
| 6,454,708 B1 | 9/2002 | Ferguson et al. |
| 6,461,305 B1 | 10/2002 | Schnall |
| 6,463,310 B1 | 10/2002 | Swedlow et al. |
| 6,466,809 B1 | 10/2002 | Riley |
| 6,468,241 B1 | 10/2002 | Gelfand et al. |
| 6,470,199 B1 | 10/2002 | Kopotic et al. |
| 6,470,279 B1 | 10/2002 | Samsoondar |
| 6,480,762 B1 | 11/2002 | Uchikubo et al. |
| 6,491,638 B2 | 12/2002 | Oka |
| 6,491,639 B1 | 12/2002 | Turcott |
| 6,503,087 B1 | 1/2003 | Eggert et al. |
| 6,503,204 B1 | 1/2003 | Sumanaweera et al. |
| 6,505,061 B2 | 1/2003 | Larson |
| 6,511,478 B1 | 1/2003 | Burnside et al. |
| 6,516,289 B2 | 2/2003 | David |
| 6,524,257 B2 | 2/2003 | Ogura |
| 6,525,386 B1 | 2/2003 | Mills et al. |
| 6,526,309 B1 | 2/2003 | Chance |
| 6,526,970 B2 | 3/2003 | DeVries et al. |
| 6,527,725 B1 | 3/2003 | Inukai et al. |
| 6,527,726 B2 | 3/2003 | Goto et al. |
| 6,535,765 B1 | 3/2003 | Amely-Velez et al. |
| 6,537,220 B1 | 3/2003 | Friemel et al. |
| 6,541,756 B2 | 4/2003 | Schulz et al. |
| 6,542,081 B2 | 4/2003 | Torch |
| 6,547,742 B2 | 4/2003 | Oka et al. |
| 6,547,743 B2 | 4/2003 | Brydon |
| 6,551,252 B2 | 4/2003 | Sackner et al. |
| 6,553,242 B1 | 4/2003 | Sarussi |
| 6,553,243 B2 | 4/2003 | Gurley |
| 6,575,902 B1 | 6/2003 | Burton |
| 6,575,904 B2 | 6/2003 | Nagai et al. |
| 6,580,086 B1 | 6/2003 | Schulz et al. |
| 6,582,371 B2 | 6/2003 | Miller |
| 6,582,374 B2 | 6/2003 | Yokozeki |
| 6,584,356 B2 | 6/2003 | Wassmund et al. |
| 6,589,171 B2 | 7/2003 | Keirsbilck |
| 6,589,183 B2 | 7/2003 | Yokozeki |
| 6,589,189 B2 | 7/2003 | Meyerson et al. |
| 6,594,513 B1 | 7/2003 | Jobsis et al. |
| 6,594,518 B1 * | 7/2003 | Benaron et al. ............... 600/477 |
| 6,596,016 B1 * | 7/2003 | Vreman et al. .................. 607/88 |
| 6,597,933 B2 | 7/2003 | Kiani et al. |
| 6,605,038 B1 | 8/2003 | Teller et al. |
| 6,606,512 B2 | 8/2003 | Muz et al. |
| 6,606,993 B1 | 8/2003 | Wiesmann et al. |
| 6,611,793 B1 | 8/2003 | Burnside et al. |
| 6,615,065 B1 | 9/2003 | Barrett et al. |
| 6,635,048 B1 | 10/2003 | Ullestad et al. |
| 6,640,116 B2 | 10/2003 | Diab |
| 6,645,154 B2 | 11/2003 | Oka |
| 6,645,155 B2 | 11/2003 | Inukai et al. |
| 6,653,557 B2 | 11/2003 | Wolf et al. |
| 6,654,622 B1 | 11/2003 | Eberhard et al. |
| 6,662,033 B2 | 12/2003 | Casciani et al. |
| 6,666,860 B1 | 12/2003 | Takahashi |
| 6,671,531 B2 | 12/2003 | Al-Ali et al. |
| 6,671,545 B2 | 12/2003 | Fincke |
| 6,678,543 B2 | 1/2004 | Diab et al. |
| 6,681,454 B2 | 1/2004 | Modgil et al. |
| 6,684,091 B2 | 1/2004 | Parker |
| 6,694,160 B2 | 2/2004 | Chin |
| 6,695,806 B2 | 2/2004 | Gelfand et al. |
| 6,700,497 B2 | 3/2004 | Hibbs et al. |
| 6,704,601 B1 | 3/2004 | Amely-Velez et al. |
| 6,708,048 B1 | 3/2004 | Chance |
| 6,711,425 B1 | 3/2004 | Reuss |
| 6,712,767 B2 | 3/2004 | Hossack et al. |
| 6,721,585 B1 | 4/2004 | Parker |
| 6,721,602 B2 | 4/2004 | Engmark et al. |
| 6,725,075 B2 | 4/2004 | Al-Ali |
| 6,726,327 B2 | 4/2004 | Torrey et al. |
| 6,735,459 B2 | 5/2004 | Parker |

(56) References Cited

U.S. PATENT DOCUMENTS

| | | | |
|---|---|---|---|
| 6,736,759 B1 | 5/2004 | Stubbs et al. |
| 6,736,786 B1 | 5/2004 | Shabty et al. |
| 6,743,173 B2 | 6/2004 | Penner et al. |
| 6,743,202 B2 | 6/2004 | Hirschman et al. |
| 6,745,061 B1 | 6/2004 | Hicks et al. |
| 6,748,262 B2 | 6/2004 | Harada et al. |
| 6,749,567 B2 | 6/2004 | Davis |
| 6,755,789 B2 | 6/2004 | Stringer et al. |
| 6,758,808 B2 | 7/2004 | Paul |
| 6,763,255 B2 | 7/2004 | DeLonzor et al. |
| 6,767,330 B2 | 7/2004 | Lavery |
| 6,771,994 B2 | 8/2004 | Kiani et al. |
| 6,776,758 B2 | 8/2004 | Peszynski et al. |
| 6,779,257 B2 | 8/2004 | Kiepen et al. |
| 6,785,568 B2 | 8/2004 | Chance |
| 6,792,300 B1 | 9/2004 | Diab et al. |
| 6,796,946 B2 | 9/2004 | Ogura et al. |
| 6,801,799 B2 | 10/2004 | Mendelson |
| 6,804,543 B2 | 10/2004 | Miller et al. |
| 6,804,558 B2 | 10/2004 | Haller et al. |
| 6,808,496 B2 | 10/2004 | Oka et al. |
| 6,811,538 B2 | 11/2004 | Westbrook et al. |
| 6,813,511 B2 | 11/2004 | Diab et al. |
| 6,824,520 B2 | 11/2004 | Orr et al. |
| 6,827,688 B2 | 12/2004 | Goto et al. |
| 6,829,003 B2 | 12/2004 | Takami |
| 6,830,711 B2 | 12/2004 | Mills et al. |
| 6,832,987 B2 | 12/2004 | David et al. |
| 6,842,722 B2 | 1/2005 | David |
| 6,847,294 B1 | 1/2005 | Lin et al. |
| 6,849,074 B2 | 2/2005 | Chen et al. |
| 6,853,304 B2 | 2/2005 | Reisman et al. |
| 6,870,479 B2 | 3/2005 | Gabriel |
| 6,875,176 B2 | 4/2005 | Mourad et al. |
| 6,877,511 B2 | 4/2005 | DeVries et al. |
| 6,893,400 B2 | 5/2005 | Kawaguchi et al. |
| 6,898,299 B1 | 5/2005 | Brooks |
| 6,899,682 B2 | 5/2005 | Eberle et al. |
| 6,899,684 B2 | 5/2005 | Mault et al. |
| 6,904,124 B2 | 6/2005 | Staver et al. |
| 6,907,284 B1 | 6/2005 | Hamilton et al. |
| 6,909,912 B2 | 6/2005 | Melker |
| 6,911,027 B1 | 6/2005 | Edwards et al. |
| 6,915,167 B2 | 7/2005 | Splett et al. |
| 6,920,345 B2 | 7/2005 | Al-Ali et al. |
| 6,921,198 B2 | 7/2005 | Gruszecki et al. |
| 6,923,771 B2 | 8/2005 | Ogura et al. |
| 6,923,776 B2 | 8/2005 | Shabty et al. |
| 6,930,608 B2 | 8/2005 | Grajales et al. |
| 6,934,570 B2 | 8/2005 | Kiani et al. |
| 6,934,571 B2 | 8/2005 | Wiesmann et al. |
| 6,936,011 B2 | 8/2005 | Sheldon |
| 6,938,488 B2 | 9/2005 | Diaz et al. |
| 6,939,314 B2 | 9/2005 | Hall et al. |
| 6,943,881 B2 | 9/2005 | Wang |
| 6,944,498 B2 | 9/2005 | Owen et al. |
| 6,952,870 B2 | 10/2005 | Miller |
| 6,955,650 B2 | 10/2005 | Mault et al. |
| 6,965,071 B2 | 11/2005 | Watchko et al. |
| 6,971,790 B2 | 12/2005 | Quinn et al. |
| 6,979,329 B2 | 12/2005 | Burnside et al. |
| 6,985,763 B2 | 1/2006 | Boas et al. |
| 6,985,764 B2 | 1/2006 | Mason et al. |
| 6,990,371 B2 | 1/2006 | Powers et al. |
| 6,993,371 B2 | 1/2006 | Kiani et al. |
| 6,995,665 B2 | 2/2006 | Appelt et al. |
| 7,001,334 B2 | 2/2006 | Reed et al. |
| 7,017,420 B2 | 3/2006 | Kalvesten et al. |
| 7,018,338 B2 | 3/2006 | Vetter et al. |
| 7,019,392 B2 | 3/2006 | Iwasaki |
| 7,020,508 B2 | 3/2006 | Stivoric et al. |
| 7,024,235 B2 | 4/2006 | Melker et al. |
| 7,027,850 B2 | 4/2006 | Wasserman |
| 7,027,871 B2 | 4/2006 | Burnes et al. |
| 7,033,316 B2 | 4/2006 | Takahashi |
| 7,039,449 B2 | 5/2006 | Al-Ali |
| 7,041,121 B1 | 5/2006 | Williams et al. |
| 7,047,054 B2 | 5/2006 | Benni |
| 7,047,055 B2 | 5/2006 | Boas et al. |
| 7,047,056 B2 | 5/2006 | Hannula et al. |
| 7,048,687 B1 | 5/2006 | Reuss et al. |
| 7,052,509 B2 | 5/2006 | Lennox |
| 7,054,453 B2 | 5/2006 | Causevic et al. |
| 7,054,454 B2 | 5/2006 | Causevic et al. |
| 7,063,669 B2 | 6/2006 | Brawner et al. |
| 7,067,893 B2 | 6/2006 | Mills et al. |
| 7,072,704 B2 | 7/2006 | Bucholz |
| 7,079,036 B2 | 7/2006 | Cooper et al. |
| 7,081,128 B2 | 7/2006 | Hart et al. |
| 7,085,597 B2 | 8/2006 | Fein et al. |
| 7,087,023 B2 | 8/2006 | Daft et al. |
| 7,089,061 B2 | 8/2006 | Grey |
| 7,096,052 B2 | 8/2006 | Mason et al. |
| 7,096,054 B2 | 8/2006 | Abdul-Hafiz et al. |
| 7,097,621 B2 | 8/2006 | Narimatsu et al. |
| 7,107,706 B1 | 9/2006 | Bailey |
| 7,108,659 B2 | 9/2006 | Ross |
| 7,112,196 B2 | 9/2006 | Brosch et al. |
| RE39,359 E | 10/2006 | McGraw et al. |
| 7,122,005 B2 | 10/2006 | Shusterman |
| 7,125,383 B2 | 10/2006 | Hoctor et al. |
| 7,127,278 B2 | 10/2006 | Melker et al. |
| 7,132,641 B2 | 11/2006 | Schulz et al. |
| 7,136,452 B2 | 11/2006 | Spartiotis et al. |
| 7,158,822 B2 | 1/2007 | Payne, Jr. |
| 7,160,284 B2 | 1/2007 | Ullestad et al. |
| 7,161,484 B2 | 1/2007 | Tsoukalis |
| 7,164,938 B2 | 1/2007 | Geddes et al. |
| 7,167,743 B2 | 1/2007 | Heruth et al. |
| 7,171,251 B2 | 1/2007 | Sarussi et al. |
| 7,179,228 B2 | 2/2007 | Banet |
| 7,181,264 B2 | 2/2007 | Wiesmann et al. |
| 7,181,505 B2 | 2/2007 | Haller et al. |
| 7,190,986 B1 * | 3/2007 | Hannula et al. ............... 600/344 |
| 7,190,987 B2 | 3/2007 | Lindekugel |
| 7,192,403 B2 | 3/2007 | Russell et al. |
| 7,197,357 B2 | 3/2007 | Istvan et al. |
| 7,198,605 B2 | 4/2007 | Donofrio et al. |
| 7,204,250 B1 | 4/2007 | Burton |
| 7,214,191 B2 | 5/2007 | Stringer et al. |
| 7,218,232 B2 | 5/2007 | DiSilvestro et al. |
| 7,220,220 B2 | 5/2007 | Stubbs et al. |
| 7,222,624 B2 | 5/2007 | Rashad |
| 7,224,282 B2 | 5/2007 | Terauchi et al. |
| 7,225,006 B2 | 5/2007 | Al-Ali et al. |
| 7,225,007 B2 | 5/2007 | Al-Ali et al. |
| 7,229,400 B2 | 6/2007 | Elliott et al. |
| 7,245,953 B1 | 7/2007 | Parker |
| 7,248,905 B2 | 7/2007 | Fukuda et al. |
| 7,248,910 B2 | 7/2007 | Li et al. |
| 7,254,444 B2 | 8/2007 | Moore et al. |
| 7,255,475 B2 | 8/2007 | Quinn et al. |
| 7,257,448 B2 | 8/2007 | Crowe et al. |
| 7,263,393 B2 | 8/2007 | Smith et al. |
| 7,270,636 B2 | 9/2007 | Lin et al. |
| 7,280,858 B2 | 10/2007 | Al-Ali et al. |
| 7,289,837 B2 | 10/2007 | Mannheimer et al. |
| 7,297,119 B2 | 11/2007 | Westbrook et al. |
| 7,303,680 B2 | 12/2007 | Connell et al. |
| 7,313,427 B2 | 12/2007 | Benni |
| 7,349,726 B2 | 3/2008 | Casciani et al. |
| 7,376,454 B2 | 5/2008 | Casciani et al. |
| 7,413,305 B2 | 8/2008 | Baumann et al. |
| 7,415,298 B2 | 8/2008 | Casciani et al. |
| 7,556,601 B2 * | 7/2009 | Branch et al. ............... 600/245 |
| 7,636,594 B2 * | 12/2009 | Watson, Jr. ............... 600/323 |
| 2001/0000790 A1 | 5/2001 | Delonzor et al. |
| 2001/0009398 A1 | 7/2001 | Sekura et al. |
| 2002/0013538 A1 | 1/2002 | Teller |
| 2002/0042558 A1 | 4/2002 | Mendelson |
| 2002/0052539 A1 | 5/2002 | Haller et al. |
| 2002/0084904 A1 | 7/2002 | De La Huerga |
| 2002/0091335 A1 | 7/2002 | John et al. |
| 2002/0095092 A1 | 7/2002 | Kondo et al. |

(56) References Cited

U.S. PATENT DOCUMENTS

| | | |
|---|---|---|
| 2002/0103445 A1 | 8/2002 | Rahdert et al. |
| 2002/0109600 A1 | 8/2002 | Mault et al. |
| 2002/0124295 A1 | 9/2002 | Fenwick et al. |
| 2002/0139368 A1 | 10/2002 | Bachinski |
| 2002/0148470 A1 | 10/2002 | Blue et al. |
| 2002/0151929 A1 | 10/2002 | Goto et al. |
| 2002/0156354 A1 | 10/2002 | Larson |
| 2002/0161309 A1 | 10/2002 | Marro |
| 2002/0173706 A1 | 11/2002 | Takatani et al. |
| 2002/0173708 A1 | 11/2002 | DeLonzor et al. |
| 2003/0004547 A1 | 1/2003 | Owen et al. |
| 2003/0009119 A1 | 1/2003 | Kamm et al. |
| 2003/0009308 A1 | 1/2003 | Kirtley |
| 2003/0023140 A1 | 1/2003 | Chance |
| 2003/0036685 A1 | 2/2003 | Goodman |
| 2003/0065275 A1 | 4/2003 | Mault et al. |
| 2003/0086156 A1 | 5/2003 | McGuire |
| 2003/0120183 A1 | 6/2003 | Simmons |
| 2003/0122706 A1 | 7/2003 | Choi et al. |
| 2003/0125616 A1 | 7/2003 | Black et al. |
| 2003/0135127 A1 | 7/2003 | Sackner et al. |
| 2003/0144579 A1 | 7/2003 | Buss |
| 2003/0156288 A1 | 8/2003 | Barnum et al. |
| 2003/0171662 A1 | 9/2003 | O'Connor et al. |
| 2003/0176810 A1 | 9/2003 | Maahs et al. |
| 2003/0189492 A1 | 10/2003 | Harvie |
| 2003/0216728 A1 | 11/2003 | Stern et al. |
| 2003/0225323 A1 | 12/2003 | Kiani et al. |
| 2004/0002655 A1 | 1/2004 | Bolorforosh et al. |
| 2004/0007585 A1 | 1/2004 | Griffith et al. |
| 2004/0030258 A1 | 2/2004 | Williams et al. |
| 2004/0044545 A1 | 3/2004 | Wiesmann et al. |
| 2004/0054287 A1 | 3/2004 | Stephens |
| 2004/0054291 A1 | 3/2004 | Schulz et al. |
| 2004/0064097 A1 | 4/2004 | Peterson |
| 2004/0064165 A1 | 4/2004 | Thompson |
| 2004/0082842 A1 | 4/2004 | Lumba et al. |
| 2004/0092919 A1 | 5/2004 | Ritchie et al. |
| 2004/0100784 A1 | 5/2004 | Willers et al. |
| 2004/0102931 A1 | 5/2004 | Ellis et al. |
| 2004/0117891 A1 | 6/2004 | Hannula et al. |
| 2004/0144391 A1 | 7/2004 | Brady et al. |
| 2004/0147821 A1 | 7/2004 | Al-Ali et al. |
| 2004/0147974 A1 | 7/2004 | Engmark et al. |
| 2004/0149282 A1 | 8/2004 | Hickle |
| 2004/0163648 A1 | 8/2004 | Burton |
| 2004/0173456 A1 | 9/2004 | Boos et al. |
| 2004/0221370 A1 | 11/2004 | Hannula et al. |
| 2004/0230116 A1 | 11/2004 | Cowan et al. |
| 2004/0231772 A1 | 11/2004 | Leonard et al. |
| 2004/0236207 A1 | 11/2004 | Widener et al. |
| 2004/0236242 A1 | 11/2004 | Graham et al. |
| 2004/0242981 A1 | 12/2004 | Pattisapu |
| 2004/0254490 A1 | 12/2004 | Egli |
| 2004/0254501 A1 | 12/2004 | Mault |
| 2004/0267145 A1 | 12/2004 | David et al. |
| 2005/0001728 A1 | 1/2005 | Appelt et al. |
| 2005/0020919 A1 | 1/2005 | Stringer et al. |
| 2005/0027207 A1 | 2/2005 | Westbrook et al. |
| 2005/0029432 A1 | 2/2005 | Bacarella et al. |
| 2005/0041531 A1 | 2/2005 | Sekura et al. |
| 2005/0043599 A1 | 2/2005 | O'Mara |
| 2005/0043600 A1 | 2/2005 | Diab et al. |
| 2005/0043763 A1 | 2/2005 | Marcovecchio et al. |
| 2005/0049465 A1 | 3/2005 | Wang |
| 2005/0049501 A1 | 3/2005 | Conero et al. |
| 2005/0059869 A1 | 3/2005 | Scharf et al. |
| 2005/0070776 A1 | 3/2005 | Mannheimer et al. |
| 2005/0070778 A1 | 3/2005 | Lackey et al. |
| 2005/0075550 A1 | 4/2005 | Lindekugel |
| 2005/0080345 A1 | 4/2005 | Finburgh et al. |
| 2005/0085799 A1 | 4/2005 | Luria et al. |
| 2005/0090754 A1 | 4/2005 | Wolff et al. |
| 2005/0096557 A1 | 5/2005 | Vosburgh et al. |
| 2005/0101845 A1 | 5/2005 | Nihtila |
| 2005/0102167 A1 | 5/2005 | Kapoor |
| 2005/0113650 A1 | 5/2005 | Pacione et al. |
| 2005/0113656 A1 | 5/2005 | Chance |
| 2005/0113703 A1 | 5/2005 | Farringdon et al. |
| 2005/0114154 A1 | 5/2005 | Wolkoweiz et al. |
| 2005/0163412 A1 | 7/2005 | Glebov |
| 2005/0171576 A1 | 8/2005 | Williams et al. |
| 2005/0182458 A1 | 8/2005 | Goedeke |
| 2005/0188991 A1 | 9/2005 | Sun et al. |
| 2005/0190068 A1 | 9/2005 | Gentry et al. |
| 2005/0197548 A1 | 9/2005 | Dietiker |
| 2005/0206518 A1 | 9/2005 | Welch et al. |
| 2005/0215847 A1 | 9/2005 | Heruth et al. |
| 2005/0215880 A1 | 9/2005 | Harrison et al. |
| 2005/0215947 A1 | 9/2005 | Heruth et al. |
| 2005/0216064 A1 | 9/2005 | Heruth et al. |
| 2005/0216199 A1 | 9/2005 | Banet |
| 2005/0222522 A1 | 10/2005 | Heruth et al. |
| 2005/0228234 A1 | 10/2005 | Yang |
| 2005/0228248 A1 | 10/2005 | Dietiker |
| 2005/0228297 A1 | 10/2005 | Banet et al. |
| 2005/0228299 A1 | 10/2005 | Banet et al. |
| 2005/0231686 A1 | 10/2005 | Rathjen |
| 2005/0234312 A1 | 10/2005 | Suzuki et al. |
| 2005/0234317 A1 | 10/2005 | Kiani |
| 2005/0234518 A1 | 10/2005 | Heruth et al. |
| 2005/0240087 A1 | 10/2005 | Keenan et al. |
| 2005/0256523 A1 | 11/2005 | Chen et al. |
| 2005/0261594 A1 | 11/2005 | Banet |
| 2005/0268916 A1 | 12/2005 | Mumford et al. |
| 2005/0277819 A1 | 12/2005 | Kiani et al. |
| 2006/0009685 A1 | 1/2006 | Finarov et al. |
| 2006/0009698 A1 | 1/2006 | Banet et al. |
| 2006/0020181 A1 | 1/2006 | Schmitt |
| 2006/0030049 A1 | 2/2006 | Bhimani et al. |
| 2006/0030767 A1 | 2/2006 | Lang et al. |
| 2006/0036179 A1 | 2/2006 | Miller |
| 2006/0047447 A1 | 3/2006 | Brady et al. |
| 2006/0058593 A1 | 3/2006 | Drinan et al. |
| 2006/0058690 A1 | 3/2006 | Bartnik et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0074280 A1 | 4/2006 | Martis et al. |
| 2006/0074283 A1 | 4/2006 | Henderson et al. |
| 2006/0074324 A1 | 4/2006 | Wu et al. |
| 2006/0075257 A1 | 4/2006 | Martis et al. |
| 2006/0079794 A1 | 4/2006 | Liu et al. |
| 2006/0084848 A1 | 4/2006 | Mitchnick |
| 2006/0084852 A1 | 4/2006 | Mason et al. |
| 2006/0085227 A1 | 4/2006 | Rosenfeld et al. |
| 2006/0095032 A1 | 5/2006 | Jackson et al. |
| 2006/0100496 A1 | 5/2006 | Avron |
| 2006/0100530 A1 | 5/2006 | Kliot et al. |
| 2006/0100618 A1 | 5/2006 | Chan et al. |
| 2006/0122517 A1 | 6/2006 | Banet et al. |
| 2006/0122520 A1 | 6/2006 | Banet et al. |
| 2006/0124128 A1 | 6/2006 | Deane et al. |
| 2006/0125623 A1 | 6/2006 | Appelt et al. |
| 2006/0129039 A1 | 6/2006 | Lindner et al. |
| 2006/0132382 A1 | 6/2006 | Jannard |
| 2006/0133362 A1 | 6/2006 | Stein et al. |
| 2006/0142640 A1 | 6/2006 | Takahashi |
| 2006/0149132 A1 | 7/2006 | Iddan |
| 2006/0149339 A1 | 7/2006 | Burnes et al. |
| 2006/0167351 A1 | 7/2006 | Isaacson et al. |
| 2006/0173247 A1 | 8/2006 | Medina |
| 2006/0183980 A1 | 8/2006 | Yang |
| 2006/0184051 A1 | 8/2006 | Hempstead et al. |
| 2006/0189859 A1 | 8/2006 | Kiani et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0211942 A1 | 9/2006 | Hoctor et al. |
| 2006/0217604 A1 | 9/2006 | Fein et al. |
| 2006/0217605 A1 | 9/2006 | Fein et al. |
| 2006/0217606 A1 | 9/2006 | Fein et al. |

(56) References Cited

U.S. PATENT DOCUMENTS

| | | |
|---|---|---|
| 2006/0217607 A1 | 9/2006 | Fein et al. |
| 2006/0217608 A1 | 9/2006 | Fein et al. |
| 2006/0224040 A1 | 10/2006 | Khait et al. |
| 2006/0224326 A1 | 10/2006 | St. Ores et al. |
| 2006/0224421 A1 | 10/2006 | St. Ores et al. |
| 2006/0229510 A1 | 10/2006 | Fein et al. |
| 2006/0229511 A1 | 10/2006 | Fein et al. |
| 2006/0241358 A1 | 10/2006 | Al-Ali et al. |
| 2006/0241384 A1 | 10/2006 | Fisher et al. |
| 2006/0241510 A1 | 10/2006 | Halperin et al. |
| 2006/0247504 A1 | 11/2006 | Tice |
| 2006/0253953 A1 | 11/2006 | Williams |
| 2006/0258922 A1 | 11/2006 | Mason et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0264726 A1 | 11/2006 | Mannheimer et al. |
| 2006/0264727 A1 | 11/2006 | Mannheimer et al. |
| 2006/0264771 A1 | 11/2006 | Lin et al. |
| 2006/0276701 A1 | 12/2006 | Ray |
| 2006/0281984 A1 | 12/2006 | Mannheimer et al. |
| 2007/0032732 A1 | 2/2007 | Shelley et al. |
| 2007/0060808 A1 | 3/2007 | Hoarau |
| 2007/0073117 A1 | 3/2007 | Raridan, Jr. |
| 2007/0073121 A1 | 3/2007 | Hoarau et al. |
| 2007/0073123 A1 | 3/2007 | Raridan, Jr. |
| 2007/0073126 A1 | 3/2007 | Raridan, Jr. |
| 2007/0078316 A1 | 4/2007 | Hoarau |
| 2007/0100218 A1 | 5/2007 | Sweitzer et al. |
| 2007/0100219 A1 | 5/2007 | Sweitzer et al. |
| 2007/0106132 A1 | 5/2007 | Elhag et al. |
| 2007/0129622 A1 | 6/2007 | Bourget et al. |
| 2007/0149871 A1 | 6/2007 | Sarussi et al. |
| 2007/0260129 A1 | 11/2007 | Chin et al. |
| 2007/0260130 A1 | 11/2007 | Chin |
| 2007/0293746 A1 | 12/2007 | Sarussi et al. |
| 2008/0009691 A1 | 1/2008 | Parker |
| 2008/0076980 A1 | 3/2008 | Hoarau |
| 2008/0076981 A1 | 3/2008 | Hoarau |
| 2008/0076988 A1 | 3/2008 | Sarussi et al. |
| 2008/0076990 A1 | 3/2008 | Sarussi et al. |
| 2008/0076993 A1 | 3/2008 | Ostrowski |
| 2008/0076994 A1 | 3/2008 | Hoarau |
| 2008/0076996 A1 | 3/2008 | Hoarau |
| 2008/0081967 A1 | 4/2008 | Andersohn et al. |
| 2008/0139908 A1 | 6/2008 | Kurth |
| 2008/0143080 A1 | 6/2008 | Burr |
| 2008/0146890 A1 | 6/2008 | Leboeuf et al. |
| 2008/0165017 A1 | 7/2008 | Schwartz |
| 2008/0177163 A1 | 7/2008 | Wang et al. |
| 2008/0221413 A1 | 9/2008 | Hoarau |
| 2008/0221414 A1 | 9/2008 | Baker |
| 2008/0227349 A1 | 9/2008 | Eyck et al. |
| 2008/0228053 A1 | 9/2008 | Wang et al. |
| 2008/0230363 A1 | 9/2008 | Yang et al. |
| 2008/0316488 A1 | 12/2008 | Mao et al. |
| 2008/0319286 A1* | 12/2008 | Ridder et al. ................. 600/310 |
| 2010/0031904 A1 | 2/2010 | Matsuura et al. |
| 2010/0076337 A1* | 3/2010 | Medina ........................ 600/549 |

FOREIGN PATENT DOCUMENTS

| | | |
|---|---|---|
| DE | 3516338 | 11/1986 |
| DE | 3703458 | 8/1988 |
| DE | 3705493 | 8/1988 |
| DE | 3744781 | 1/1989 |
| DE | 3810411 | 10/1989 |
| DE | 3927038 | 2/1991 |
| DE | 4429845 | 10/1995 |
| DE | 19632361 | 2/1997 |
| DE | 19541605 | 5/1997 |
| DE | 19939302 | 5/2001 |
| DE | 10029205 | 1/2002 |
| DE | 20318882 | 4/2004 |
| EP | 0127947 | 12/1984 |
| EP | 0204259 | 12/1986 |
| EP | 268850 | 6/1988 |
| EP | 0313238 | 4/1989 |
| EP | 338518 | 10/1989 |
| EP | 430340 | 6/1991 |
| EP | 463620 | 1/1992 |
| EP | 0531631 | 3/1993 |
| EP | 543172 | 5/1993 |
| EP | 0572684 | 12/1993 |
| EP | 0573137 | 12/1993 |
| EP | 578530 | 1/1994 |
| EP | 580385 | 1/1994 |
| EP | 775311 | 8/1994 |
| EP | 621026 | 10/1994 |
| EP | 0631756 | 1/1995 |
| EP | 665025 | 8/1995 |
| EP | 0695139 | 2/1996 |
| EP | 0721110 | 7/1996 |
| EP | 1048323 | 2/2000 |
| EP | 996063 | 4/2000 |
| EP | 1130412 | 5/2001 |
| EP | 1169965 | 1/2002 |
| EP | 1683478 | 7/2006 |
| EP | 1807001 | 7/2007 |
| EP | 1961324 A1 | 8/2008 |
| FR | 2555744 | 11/1983 |
| FR | 2601137 | 1/1988 |
| FR | 2685865 | 7/1993 |
| GB | 834469 | 5/1960 |
| GB | 2135074 | 8/1984 |
| GB | 2390903 | 1/2004 |
| JP | 55024614 | 2/1980 |
| JP | 04057161 | 2/1992 |
| JP | 5049625 | 3/1993 |
| JP | 6014906 | 1/1994 |
| JP | 6269430 | 9/1994 |
| JP | 7001273 | 1/1995 |
| JP | 7155311 | 6/1995 |
| JP | 7155313 | 6/1995 |
| JP | 7236625 | 9/1995 |
| JP | 07336597 | 12/1995 |
| JP | 08111295 | 4/1996 |
| JP | 08112257 | 5/1996 |
| JP | 08336546 | 12/1996 |
| JP | 09010319 | 1/1997 |
| JP | 09154937 | 6/1997 |
| JP | 10314149 | 12/1998 |
| JP | 10337282 | 12/1998 |
| JP | 11259583 | 9/1999 |
| JP | 2000189440 | 7/2000 |
| JP | 2000237170 | 9/2000 |
| JP | 2001161648 | 6/2001 |
| JP | 2001190498 | 7/2001 |
| JP | 2001308576 | 11/2001 |
| JP | 2001332832 | 11/2001 |
| JP | 2001346775 | 12/2001 |
| JP | 2002065647 | 3/2002 |
| JP | 2003210402 | 7/2003 |
| JP | 2003235813 | 8/2003 |
| JP | 2003265425 | 9/2003 |
| JP | 2003275192 | 9/2003 |
| JP | 2004016659 | 1/2004 |
| JP | 2004065832 | 3/2004 |
| JP | 2004121549 | 4/2004 |
| JP | 2004159810 | 6/2004 |
| JP | 2004258761 | 9/2004 |
| JP | 2004337605 | 12/2004 |
| JP | 2004344367 | 12/2004 |
| JP | 2005013612 | 1/2005 |
| JP | 2005110816 | 4/2005 |
| JP | 2005111187 | 4/2005 |
| JP | 2005125106 | 5/2005 |
| JP | 2005143782 | 6/2005 |
| JP | 2005168600 | 6/2005 |
| JP | 2005266860 | 9/2005 |
| JP | 2006061178 | 3/2006 |
| JP | 2006066512 | 3/2006 |

(56) References Cited

FOREIGN PATENT DOCUMENTS

| | | |
|---|---|---|
| JP | 2006122693 | 5/2006 |
| JP | 2006297125 | 11/2006 |
| JP | 2007195816 | 8/2007 |
| JP | 2008119026 | 5/2008 |
| KR | 2003065871 | 5/2004 |
| KR | 2005106928 | 12/2004 |
| RU | 2132204 | 6/1999 |
| WO | WO9001293 | 2/1990 |
| WO | WO9111137 | 8/1991 |
| WO | WO9115151 | 10/1991 |
| WO | WO9118550 | 12/1991 |
| WO | WO9220273 | 11/1992 |
| WO | WO9502358 | 1/1995 |
| WO | WO9506430 | 3/1995 |
| WO | WO9512349 | 5/1995 |
| WO | WO9615714 | 5/1996 |
| WO | WO9616591 | 6/1996 |
| WO | WO9641138 | 12/1996 |
| WO | WO9720494 | 6/1997 |
| WO | WO9720497 | 6/1997 |
| WO | WO9736536 | 10/1997 |
| WO | WO9817174 | 4/1998 |
| WO | 98/27865 A1 | 7/1998 |
| WO | WO9947039 | 9/1999 |
| WO | WO0059374 | 10/2000 |
| WO | WO0078209 | 12/2000 |
| WO | WO0101855 | 1/2001 |
| WO | WO0117425 | 3/2001 |
| WO | WO0176471 | 10/2001 |
| WO | WO0187224 | 11/2001 |
| WO | WO0215784 | 2/2002 |
| WO | WO02065901 | 8/2002 |
| WO | WO02066977 | 8/2002 |
| WO | WO02089664 | 11/2002 |
| WO | WO03026558 | 4/2003 |
| WO | WO03057030 | 7/2003 |
| WO | WO03071928 | 9/2003 |
| WO | WO03080152 | 10/2003 |
| WO | WO2004030480 | 4/2004 |
| WO | WO2004046673 | 6/2004 |
| WO | WO2004084720 | 10/2004 |
| WO | WO2005046466 | 5/2005 |
| WO | WO2005079663 | 9/2005 |
| WO | WO2006007231 | 1/2006 |
| WO | WO2006017117 | 2/2006 |
| WO | WO2006021956 | 3/2006 |
| WO | WO2006094108 | 9/2006 |
| WO | WO2007048039 | 4/2007 |
| WO | WO2006110488 | 5/2007 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the $22^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the $22^{nd}$ Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Gosney, S., et al.; "An alternative position for the pulse oximeter probe," *Anaesthesia*, vol. 56, p. 493 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of esophageal photoplethysmographic signals and blood oxygen saturation measurements in cardiothoracic surgery patients," *Physiological Measurement*, vol. 23, No. 3, pp. 533-545 (Aug. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Kocher, Serge, et al.; "Performance of a Digital $PCO_2/SPO_2$ Ear Sensor," *Journal of Clinical Monitoring and Computing*, vol. 18, pp. 75-59 (2004).

(56) References Cited

OTHER PUBLICATIONS

International Search Report and Written Opinion for PCT Application No. PCT/US2010/027914 dated Apr. 19, 2011, 18 pgs.

Wendelken, Suzanne, et al.; "The Feasibility of Using a Forehead Reflectance Pulse Oximeter for Automated Remote Triage," *IEEE*, pp. 180-181 (2004).

Sugino, Shigekzau, et al.; "Forehead is as sensitive as finger pulse oximetry during general anesthesia," *Can J. Anesth.*; General Anesthesia, vol. 51, No. 5; pp. 432-436 (2004).

Kocher, Serge, et al.; "Performance of a Digital $PCO_2/SPO_2$ Ear Sensor," *Journal of Clinical Monitoring and Computing*, vol. 18, pp. 75-59 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

http://www.fcw.com.my/fujifilm.html; Jun. 25, 2008.

\* cited by examiner

MEDICAL SENSOR WITH FLEXIBLE COMPONENTS AND TECHNIQUE FOR USING THE SAME

CROSS-REFERENCE TO RELATED APPLICATIONS

This claims the benefit of U.S. Provisional Patent Application No. 61/165,269, filed Mar. 31, 2009, which is hereby incorporated by reference herein in its entirety.

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings involve placement of a sensor on a patient's tissue, typically via a lightly adhesive sensor, a clip-style sensor, or a sensor that may be fitted into a wearable garment, such as a hat or a headband. With regard to the latter, if the hat or headband is not closely fitted to the patient's tissue, ambient light may interfere with the sensor's light detection. Some outside light infiltration into the sensor may be avoided by fitting the sensor snugly against the patient's tissue. However, such a conforming fit may be difficult to achieve over a range of patient physiologies without adjustment or excessive attention on the part of medical personnel. Additionally, an overly tight fit may cause local exsanguination of the tissue around the sensor. Exsanguinated tissue, which is devoid of blood, may shunt the sensor light through the tissue, which may also affect measurement accuracy.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
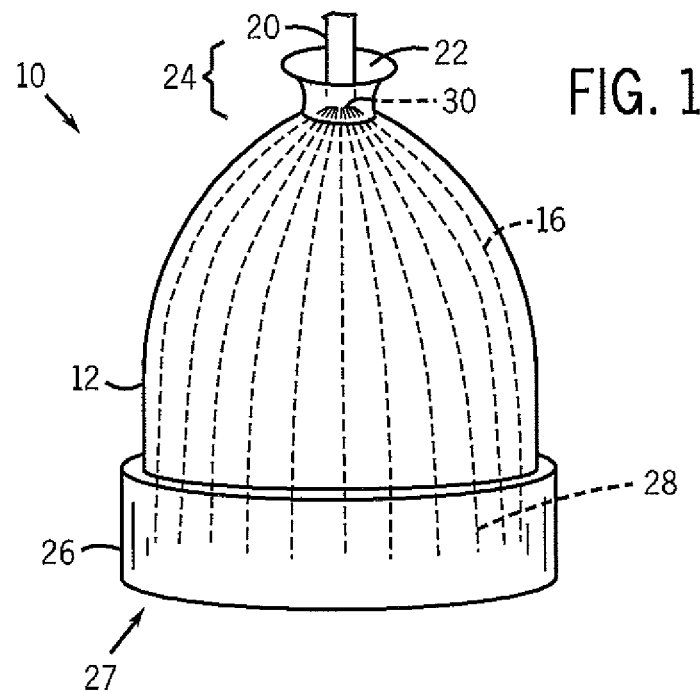
FIG. 1 illustrates a perspective view of a hat structure with multiple optical fibers for holding a medical sensor on a patient's tissue according to an embodiment.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical sensors for applications utilizing spectrophotometry are provided therein that include optical components that conform closely to a patient's tissue. Such sensors may include sensors for pulse oximetry, tissue water fraction, tissue carbon dioxide, hematocrit, or glucose, or any combination thereof. In an embodiment, a hat-based pulse medical sensor assembly for neonatal patients may be configured to provide a conforming fit without uncomfortable pressure on the tissue. Because the accuracy of spectrophotometric sensors, such as pulse oximetry sensors, may be improved when the sensor is directly in contact with the skin, it may be desirable to avoid stiff or inflexible electrical or optical components that may interfere with the fit of the hat.

Hence, provided herein are flexible, wearable sensing assemblies that include optical components that may be woven into the fabric of the wearable sensor or applied directly to the fabric of the without stiff backing materials. In an embodiment, such sensor assemblies may include optical fibers that are woven into a fabric of the sensor assembly to transmit light into a patient's tissue and return light that has passed through the tissue and is representative of a physiological constituent. Also provided herein are sensor assemblies that include optical component backing materials that are thin and/or highly flexible. Such thin and/or highly flexible materials may also provide the advantage of having gripping properties without being adhesive. Sensor assemblies may also include thin and flexible optical components, such as ultrathin light emitters and photodetectors. In embodiments, the sensor assemblies may include optical components that are flush or substantially flush with the sensor body. For example, a hat band may include a pocket in which the optical components may be placed so that the surface that contacts the tissue is generally smooth or planar.

In an embodiment, a medical sensor, such as a sensor for pulse oximetry, may be adapted for placement in a hat (for example, a neonatal stocking cap), a headband, or other wearable structure (i.e. a glove, a sock, a wristband) to apply the sensor on the body of the user.

FIG. 1 illustrates an embodiment of a sensor assembly 10 including a wearable structure, which may be a hat 12, as shown in FIG. 1. The optical components of the sensor may include optical fibers 16 that transmit light from a light emitter. The optical fibers are woven into the fabric of the hat 12. When the hat 12 is applied to the patient, the optical fibers come into contact with the skin and are able to transmit and receive light as part of a medical sensor assembly 10. As shown, the optical fibers 16 may be distributed throughout the hat, allowing for multiple sites of measurement. In embodiments, a monitor or downstream measurement device may receive signals related to multiple measurements from the sensor assembly 10 and may combine or otherwise analyze the results.

Also shown in FIG. 1 is a cable 20 for providing an electrical/optical connection for the optical fibers 16 to downstream light emitter(s) and photodetector(s) (not shown). FIG. 1 shows that the cable 20 is positioned through an opening 22 in the top 24 of the hat 12. In an embodiment, the cable 20 may be adhered or otherwise constrained in the hat 12 so that the cable generally is positioned away from the hat 12 to avoid interfering with the patient's eyesight or bothering the patient.

The optical fibers 16 may be single fibers or fiber bundles. The fibers or fiber bundles 16 may be formed from relatively flexible materials, for example a transparent plastic, such as poly(methyl methacrylate) or polystyrene with a fluoropolymer cladding. Examples of optical fibers 16 include single-mode fibers, multi-mode fibers, photonic-crystal fibers, hollow-core fibers, polarization-maintaining fibers and dual-clad fibers. Typical diameters for optical fibers 16 may be 5 to 1,000 micrometers.

In one embodiment, an individual optical fiber 16 may serve to emit light into tissue and receive the light reflected back by the tissue. In other words, each individual fiber 16 may transmit emitted light and receive reflected light. In an embodiment, a fiber bundle may include fibers that are dedicated emitting fibers (i.e., optically connected to a light source) and dedicated detecting fibers (i.e., optically connected to a photodetector). A hat 12 may be woven from an optical fiber fabric, such as Luminex® Fabric (Luminex S.P.A., Italy). In one particular implementation, the optical fibers 16 may be spaced apart within the hat 12 so alternating fibers 16 are dedicated emitting fibers and dedicated detecting fibers. In such an implementation, the spacing of the fibers 16 may reflect appropriate emitter-detector spacing for pulse oximetry applications, such as at least about 1 mm to at least about 14 mm spacing. In embodiments, the spacing may be 1 mm-8 mm or 2 mm-6 mm. For other types of medical sensors, such as water fraction sensors, the spacing distance may be larger or smaller, as appropriate.

In one implementation, the optical fibers 16 may be woven into the hat. For example, the optical fibers 16 may be woven such that generally run in the same direction, such as down the length of the hat from opening 22 towards hat band 26. The distal ends 28 of the optical fibers 16 may terminate in the band 26. It should be understood that a hat 12 as envisioned may not necessarily include a band 26. In embodiments, the hat 12 may simply include a distal opening 27, and the optical fibers 16 may terminate near or towards the distal opening 27. The optical fibers 16 may be notched, terminated, scribed, or modified, for example by a cutter during the weaving process, at an appropriate location in the hat band 26. At the top portion 24 of the hat 12, the proximal ends 30 of the optical fibers 16 may be gathered within cable 20 or may otherwise optically connect to an emitter and photodetector. During the weaving process, the proximal ends 30 of the optical fibers 16 may be left loose so that they may be later incorporated into the cable 20 or other optical connector.

Figure 2:
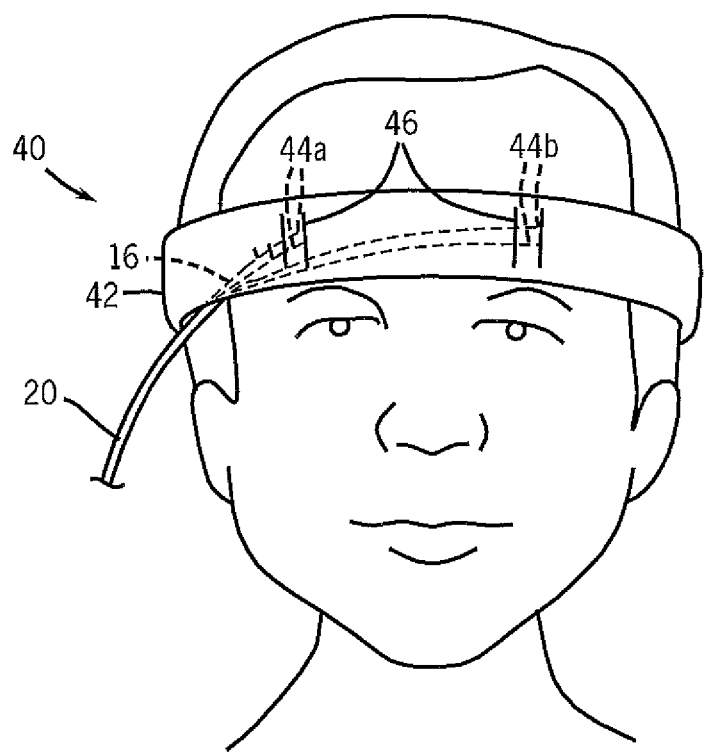
FIG. 2 illustrates a perspective view of a headband-style sensor for holding a medical sensor on a patient's tissue according to an embodiment.

While hat-based sensor assemblies 10 may generally be used on neonatal patients, adult patients may more typically wear forehead sensors that are applied directly to the forehead or sensors that are integrated into a headband. Hat-based sensors may be designed to apply light pressure to the head of an infant. In contrast, headband-based sensors may be designed to apply more pressure to the more robust tissue of an adult, which may facilitate a more conforming fit of the sensor and more accurate measurements. FIG. 2 illustrates an embodiment of a headband-based sensor assembly 40. The headband-based sensor assembly 40 may include a strap or band 42 that may be fitted around a patient's forehead tissue to bring the optical fibers 16 with the tissue. The optical fibers 16 may be woven into the fabric of the band 42. In one embodiment, the band 42 may include indicators to position the distal ends 44a and 44b of the optical fibers 16 on a particular location on the patient's forehead, for example to position the distal ends 44a and 44b on the lower forehead region, above the eyebrow, above and predominantly lateral to or centered over the iris. The location of the distal ends 44a and 44b within the band 42 facilitate appropriate placement of the optical sensing components in the desired forehead location by a user. In addition, the headband-based sensor assembly 40 may include one or more alignment indices 42, for example a printed design on the band 42 visible to the caregiver, to assist in the proper placement of the distal ends 44a and 44b of the optical fibers 16 on the patient's forehead.

Figure 3:
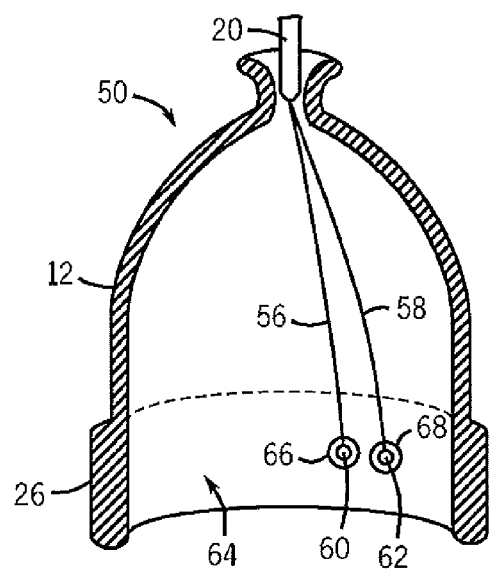
FIG. 3 is a cutaway view of the interior of a hat structure with optical sensing components sewn or otherwise attached directly to the band of the hat according to an embodiment.

In addition to using optical fibers 16 to deliver light to a patient's tissue, similar advantages (e.g., flexible optical components) may be realized by fabricating the optical components, without stiff backing materials. In an embodiment shown in FIG. 3, a hat assembly 50 may include sensing components, e.g., an emitter 60 and a detector 62, that may be applied directly to the fabric surface of the hat 12. The emitter 60 and the detector 62 may be adhered to the interior, tissue-contacting, surface 64 of the hat band. In addition, leads 56 and 58 connecting the emitter 60 and the detector 62 to the cable 20 may be adhered to or woven into the fabric of the hat 12. In embodiments in which additional electrical shielding may be desirable, the emitter 60 and the detector 62 may be glued or otherwise adhered onto thin wire mesh or other thin and flexible backings 66 and 68, respectively, which may in turn be adhered to the band 26 of the hat 12. In embodiments, flexible backings 66 and 68 may be formed from any thin and flexible material, for example any flexible material less than 5 mm in thickness, less than 1 mm in thickness, or less than 0.5 mm in thickness. The material may be sufficiently flexible to conform easily to a patient's tissue.

In certain embodiments, the sensing components themselves may be formed from thin and/or flexible materials. For example, leads 56 and 58 may be formed from thin and flexible shielded wires. The emitter 60 may be an ultra-thin LED, such as a 0.25 mm LED, available from Kingbright (City of Industry, Calif.). The detector 62 may be an ultra thin-film metal-semiconductor-metal (MSM) photodetector. In embodiments, the emitter 60 and the detector 62 may protrude less than about 1 mm, or less than about 0.5 mm from the interior surface 64 of the hat band 26. In certain embodiments, the emitter 60 and the detector 62 may protrude about 0.25 mm to about 1 mm from the interior surface 64 of the hat band 26.

Figure 4:
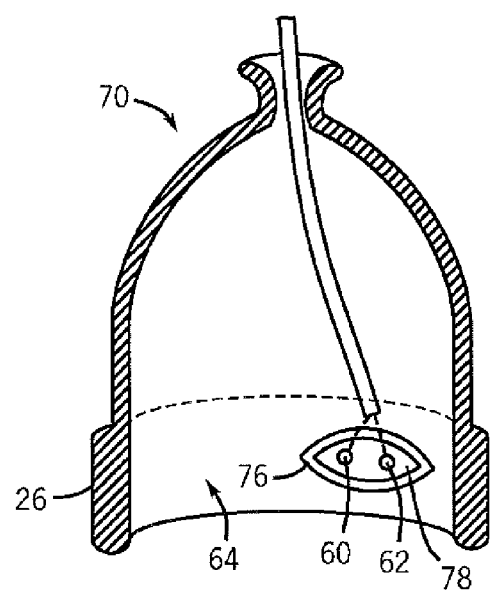
FIG. 4 is a cutaway view of the interior of a hat structure with a recess in the hat band for holding optical sensing components according to an embodiment.

A sensor assembly may also include structures, such as a pocket in the fabric, to allow the sensing components to lie flush or substantially flush against the interior surface of the hat band, which may facilitate a conforming fit against the tissue. In turn, this conforming fit may improve measurement accuracy, for example by reducing light being shunted from an emitter 60 to a detector 62. As shown in FIG. 4, a hat assembly 70 may include a buttonhole or other pocket 76 formed on the interior surface 64 of the hat band 26 that may be sized and shaped to accommodate the emitter 60 and the detector 62. In such embodiments, the emitter 60 and the detector 62 may be disposed on a thin and flexible backing, such as a fabric or paper backing 78 that is sized and shaped to fit into pocket 76 and may provide shielding to the emitter 60 and the detector 62. It should be understood that the pocket 76 may be sufficiently deep so that the emitter 60 and the detector 62 may not substantially protrude from the interior surface 64 of the hat band 26. In embodiments, the backing 78 may assist in positioning the emitter 60 and the detector 62 to lie flush with the interior surface 64 of the hat band 26.

Figure 5:
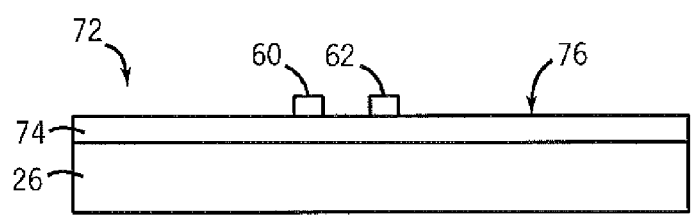
FIG. 5 is a cross-sectional view of a hat band with a gripping layer according to an embodiment.

The sensor assemblies as provided may include addition features to facilitate a secure and comfortable fit while also maintaining relatively flexible arrangements of optical sensing components. A sensor assembly 72 may include a gripping portion 74, which may be a layer applied to the interior of the hat band 26, as shown in cross-section in FIG. 5. The emitter 60 and the detector 62 may be adhered or otherwise secured to the gripping portion 74. The gripping portion 74 may be applied to the interior of a hat band 26 such that the tissue-contacting surface 76 of the gripping portion 74 may facilitate holding the sensor assembly 72 on the tissue. For example, a suitable gripping portion 74 may be made of plastic, rubber, silicone, vinyl, or woven material. In an embodiment, the gripping portion may be a relatively thin, flexible material such as Super Grip® Easy Liner® (Henkel) that is disposed on the interior of the hat 12, such as on the hat band 26.

Figure 6:
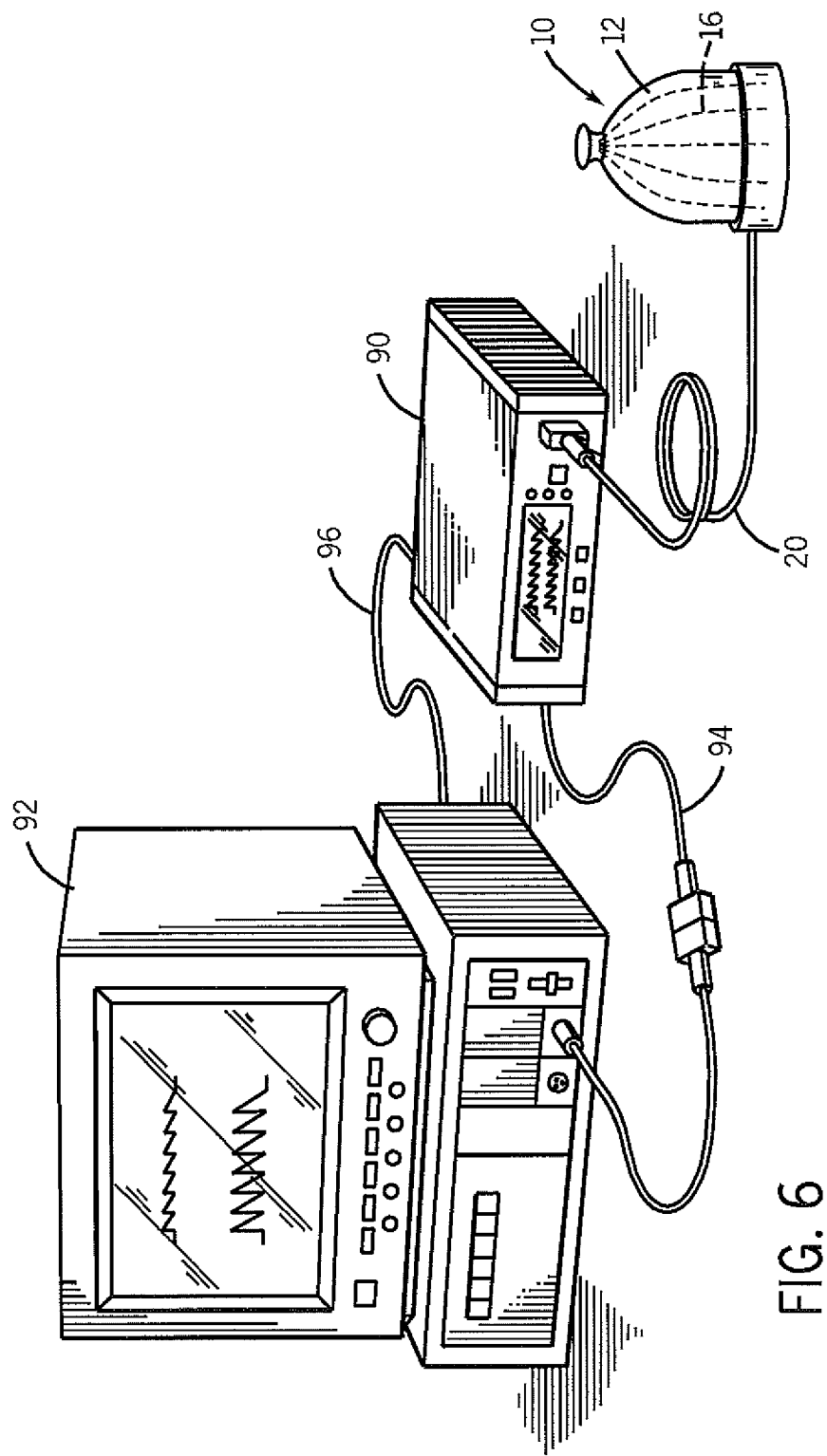
FIG. 6 illustrates a pulse oximetry system coupled to a multi-parameter patient monitor and a sensor according to an embodiment.

The gripping portion 74 may be thin and highly flexible, while also having properties such as a high coefficient of friction that may help hold the emitter 60 and the detector 62 in place. In certain embodiments, the gripping portion 74 is formed from a material that has a relatively large static coefficient of friction. A material with a large static coefficient of friction helps to keep sensor stable relative to the skin as a patient moves. The static coefficient of friction of a material may be tested using the following procedure: (1) Attach a protractor to a vertical wall with the center in line with the edge of a table. (2) Set up a stop block at the edge of the table to act as a pivot point for a glass plate. (3) Place the glass plate flat on the table with one edge along the edge of the table, up against the stop block. (4) Place a test sample of the material on the glass plate. (5) Lift the free edge of the glass plate until the test sample just starts to slip. (6) Record angle at which slippage first occurred. This angle is the angle of repose. Then calculate the coefficient of friction, which is the tangent of the angle of repose. The static coefficient of friction for gripping portion 74 may greater than 10. In certain embodiments, the static coefficient of friction for gripping portion 74 may be greater than 100. The gripping portion 74 may be a material that has a high static coefficient of friction relative to glass, such as polyvinyl chloride (PVC) foam. In embodiments, it may be desirable to calculate a static coefficient of friction of a material relative to a patient's skin. In certain embodiment, the gripping portion 74 has a static coefficient of friction greater than 5 with respect to a patient's skin The foregoing sensors and sensor assemblies provided herein may be used in conjunction with any suitable medical device. A sensor or sensor assembly, illustrated generically as a sensor assembly 10, may be used in conjunction with a pulse oximetry monitor 90, as illustrated in FIG. 6. It should be appreciated that the cable 20 of the sensor assembly 10 may be coupled to the monitor 90 or it may be coupled to a transmission device to facilitate wireless transmission between the sensor assembly 10 and the monitor 90. The monitor 90 may be any suitable pulse oximeter, such as those available from Nellcor Puritan Bennett LLC. Furthermore, to upgrade conventional pulse oximetry provided by the monitor 90 to provide additional functions, the monitor 90 may be coupled to a multi-parameter patient monitor 92 via a cable 94 connected to a sensor input port or via a cable 96 connected to a digital communication port.

Figure 7:
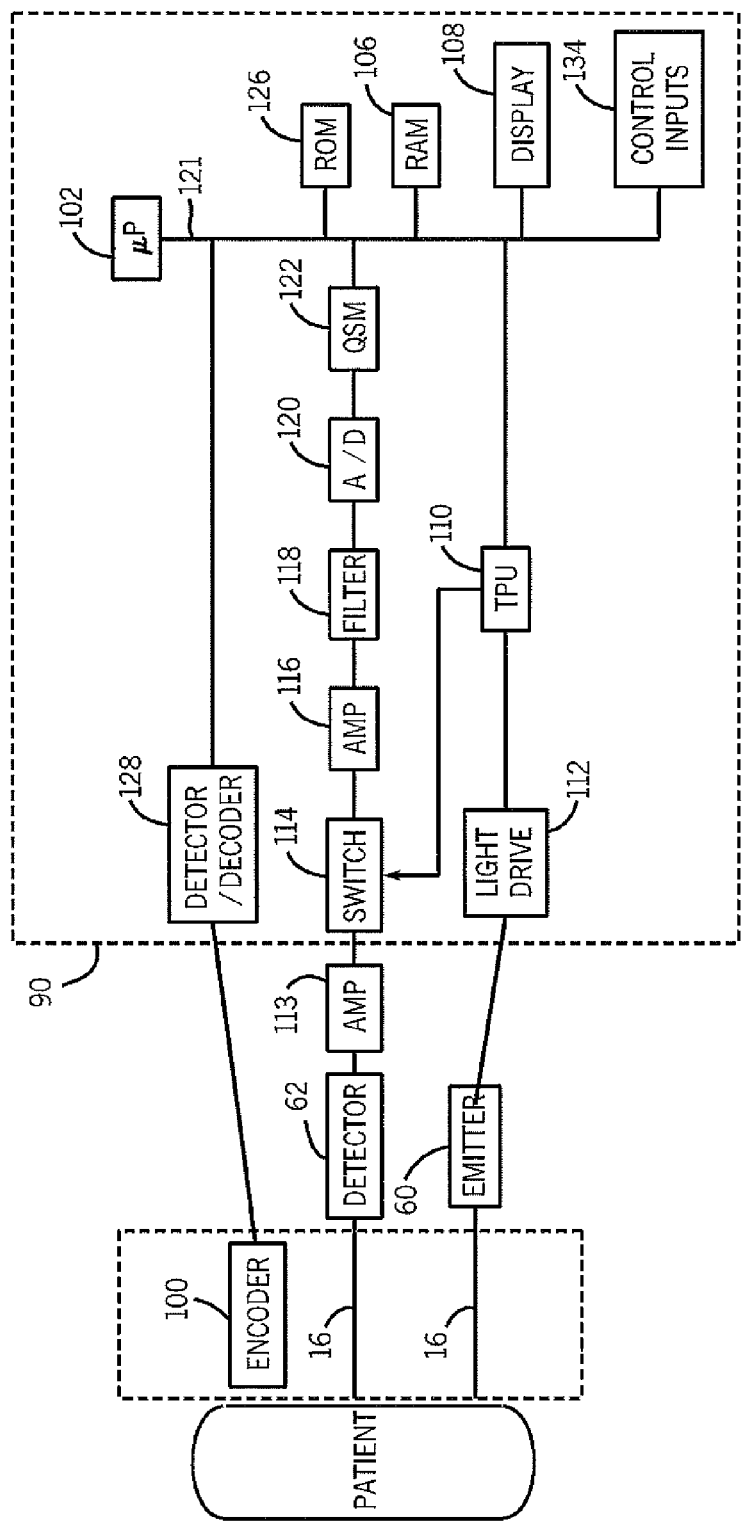
FIG. 7 is a block diagram of a pulse oximetry system according to an embodiment.

FIG. 7 is a block diagram of an embodiment of a monitor 90 that may be configured to implement the embodiments of the present disclosure. Light from optical fiber 16 (or, in embodiments in which optical fibers 16 are not used, light directly from emitter 60) may pass into a blood perfused tissue, and may be scattered, and then detected by detector 62, which may be coupled to one or more optical fibers 16. A sensor assembly 10 including optical fibers 16 (or, in embodiments, an emitter 60 and a detector 62) may also contain an encoder 100 which may be capable of providing signals indicative of the wavelength(s) of light source 60 to allow the oximeter to select appropriate calibration coefficients for calculating oxygen saturation. The encoder 100 may, in an embodiment, be a resistor or may be a storage device, such as a memory.

In an embodiment, the sensor assembly 10 may be connected to a pulse oximetry monitor 90. The monitor 90 may include a microprocessor 102 coupled to an internal bus 104. Also connected to the bus may be a RAM memory 106 and a display 108. A time processing unit (TPU) 110 may provide timing control signals to light drive circuitry 112, which controls when the emitter 60 is activated, and if multiple light sources are used the multiplexed timing for the different light sources. TPU 110 may also control the gating-in of signals from detector 62 through an amplifier 113 and a switching circuit 114. These signals are sampled at the proper time, depending at least in part upon which of multiple light sources is activated, if multiple light sources are used. The received signal from the detector 62 may be passed through an amplifier 116, a low pass filter 118, and an analog-to-digital converter 120. The digital data may then be stored in a queued serial module (QSM) 122, for later downloading to RAM 106 or ROM 126 as QSM 122 fills up.

In an embodiment, based at least in part upon the received signals corresponding to the light received by detector 62, microprocessor 122 may calculate the oxygen saturation using any suitable algorithm. Such algorithms may use coefficients, which may be empirically determined, and may correspond to the wavelengths of light used. The algorithms may be stored in a ROM 126 and accessed and operated according to microprocessor 122 instructions. For example, the encoder 100 may communicate with decoder 128 to allow the microprocessor 122 to determine the appropriate coefficients.

In an embodiment of a two-wavelength system, the particular set of coefficients chosen for any pair of wavelength spectra may be determined by a value indicated by the encoder 100 corresponding to a particular light source in a particular sensor assembly 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 134. Control inputs 134 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 may be connected to or include an emitter 60 and a detector 62 that may be of any suitable type. For example, the emitter 60 may be one or more light emitting diodes adapted to transmit one or more wavelengths of light in the red to infrared range, and the detector 62 may one or more photodetectors selected to receive light in the range or ranges emitted from the emitter 60. Alternatively, an emitter 60 may also be a laser diode or a vertical cavity surface emitting laser (VCSEL). Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

Reflectance type sensors also operate by emitting light into the tissue and detecting the light that is transmitted and scattered by the tissue. However, reflectance type sensors include an emitter 60 and detector 62 that are typically placed on the same side of the sensor site. Alternatively, side-by-side optical fibers 16 or a single multi-mode optical fiber 16 may be used for reflectance measurements. For example, a reflectance type sensor may be placed on a patient's fingertip or forehead such that the emitter 60 and detector 62 lie side-by-side. Reflectance type sensors detect light photons that are scattered back to the detector 62. A sensor assembly 10 may also be a "transflectance" sensor, such as a sensor that may subtend a portion of a baby's heel. In embodiments, contemplated sensor assemblies may be sock-type or glove-type assemblies.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A sensor comprising:
    a fabric or woven stocking cap;
    a gripping portion disposed in a band region of the stocking cap comprising a tissue-contacting surface;
    an emitter disposed on the gripping portion, wherein the emitter is configured to emit a light into a forehead region of the patient's head;
    a detector disposed on the gripping portion, wherein the detector is configured to detect the light;
    a first lead coupled to the emitter;
    a second lead coupled to the detector; and
    a cable extending from an opening in a top portion of the stocking cap and terminating in the band region, wherein the cable is coupled to the first lead and the second lead at a point spaced apart from the gripping portion.

2. The sensor of 1, wherein the gripping portion has a static coefficient of friction greater than 10.

3. The sensor of 1, wherein the gripping portion is disposed on an interior surface of a band of the stocking cap.

4. The sensor of 1, wherein the emitter and the detector are substantially flush with the tissue-contacting surface of the stocking cap.

5. A sensor comprising:
    a fabric or woven stocking cap;
    a substrate disposed in a band region of the stocking cap on a tissue-contacting surface;
    an emitter disposed on the substrate, wherein the emitter is configured to emit a light into a forehead region of the patient's head;
    a detector disposed on the substrate, wherein the detector is configured to detect the light;
    a first lead coupled to the emitter and extending outwardly from the substrate;
    a second lead coupled to the detector extending outwardly from the substrate; and
    a cable extending from an opening in a top portion of the stocking cap to the band region, wherein the cable is coupled to the first lead and the second lead in the band region at a location spaced apart from the substrate.

6. The sensor of claim 5, wherein the emitter comprises an ultra-thin LED and the detector comprises an ultra thin-film metal-semiconductor-metal (MSM) photodetector.

7. The sensor of claim 5, wherein the first lead and the second lead are adhered to the stocking cap.

8. The sensor of claim 5, wherein the first lead and the second lead are woven into the stocking cap.

9. The sensor of claim 5, wherein the first and second leads comprise flexible shielded wires.

10. The sensor of claim 5, comprising a gripping portion disposed on the tissue-contacting surface.

11. The sensor of claim 10, wherein the gripping portion has a static coefficient of friction greater than 10.

* * * * *